(12) United States Patent
Gardeski et al.

(10) Patent No.: US 7,037,290 B2
(45) Date of Patent: May 2, 2006

(54) MULTI-LUMEN STEERABLE CATHETER

(75) Inventors: Kenneth C. Gardeski, Plymouth, MN (US); Michael R. Leners, East Bethel, MN (US); Jesse T. Torbert, Cleveland Heights, OH (US); Ralph J. Thomas, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 151 days.

(21) Appl. No.: 10/318,624

(22) Filed: Dec. 16, 2002

(65) Prior Publication Data

US 2004/0116848 A1 Jun. 17, 2004

(51) Int. Cl.
*A61M 31/00* (2006.01)
(52) U.S. Cl. .................................................. 604/95.01
(58) Field of Classification Search ............. 604/95.01, 604/95.04, 528
See application file for complete search history.

(56) References Cited

U.S. PATENT DOCUMENTS

| | | | |
|---|---|---|---|
| 2,688,329 A | 9/1954 | Wallace | |
| 3,605,725 A | 9/1971 | Bentov et al. | |
| 4,586,923 A | 5/1986 | Gould et al. | |
| 4,776,844 A | 10/1988 | Ueda | |
| 5,030,204 A | 7/1991 | Badger et al. | |
| 5,368,564 A | 11/1994 | Savage | |
| 5,396,902 A | 3/1995 | Brennen et al. | |
| 5,431,168 A | 7/1995 | Webster | |
| 5,445,148 A | 8/1995 | Jaraczewski et al. | |
| 5,484,407 A * | 1/1996 | Osypka .................... | 604/95.04 |
| 5,487,757 A | 1/1996 | Truckai et al. | |
| 5,545,200 A | 8/1996 | West et al. | |
| 5,571,085 A | 11/1996 | Accisano | |
| 5,571,161 A | 11/1996 | Starksen | |
| 5,738,742 A | 4/1998 | Stevens | |
| 5,823,955 A | 10/1998 | Kuck et al. | |
| 5,873,842 A | 2/1999 | Brennen et al. | |
| 5,882,333 A | 3/1999 | Schaer et al. | |
| 5,964,971 A | 10/1999 | Lunn | |
| 6,002,955 A | 12/1999 | Willems et al. | |
| 6,004,310 A | 12/1999 | Bardsley et al. | |
| 6,146,338 A | 11/2000 | Gardeski et al. | |
| 6,217,549 B1 | 4/2001 | Selmon et al. | |
| 6,251,092 B1 | 6/2001 | Qin et al. | |
| 6,371,476 B1 | 4/2002 | Isogal et al. | |
| 2001/0049491 A1 | 12/2001 | Shimada | |

\* cited by examiner

*Primary Examiner*—Kevin C. Simons
(74) *Attorney, Agent, or Firm*—Michael C. Soldner; Girma Wolde-Michael

(57) ABSTRACT

Elongated medical devices are disclosed adapted to be inserted through an access pathway into a body vessel, organ or cavity to locate a therapeutic or diagnostic distal segment of the elongated medical device into alignment with an anatomic feature of interest. Multi-lumen steerable catheters having a deflection lumen liner and a delivery lumen liner are adapted to be deflected by a deflection mechanism within or advanced through the deflection lumen liner to enable advancement of the catheter distal end through a tortuous pathway. At least one lumen liner is formed of a no yield elastomer.

17 Claims, 7 Drawing Sheets

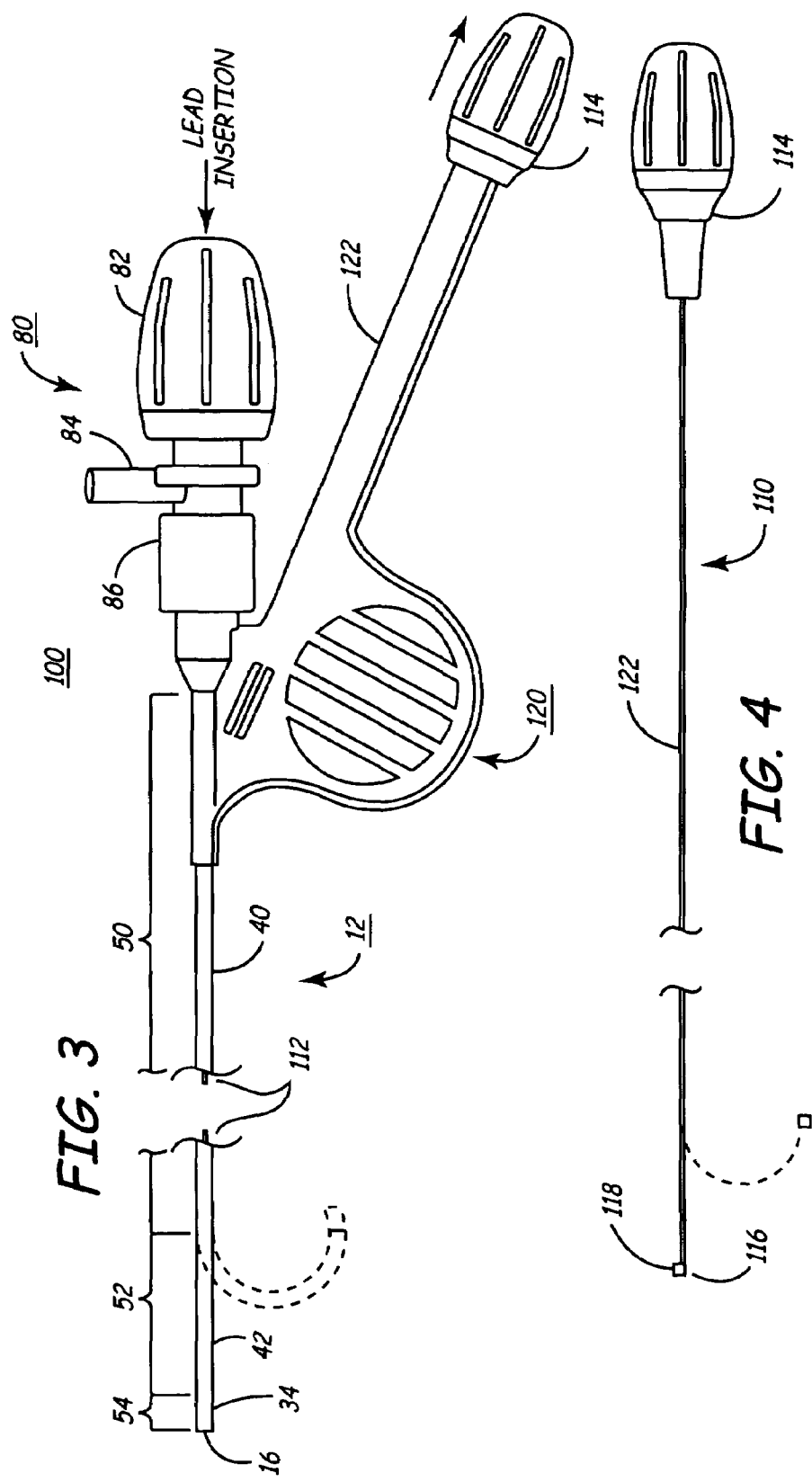

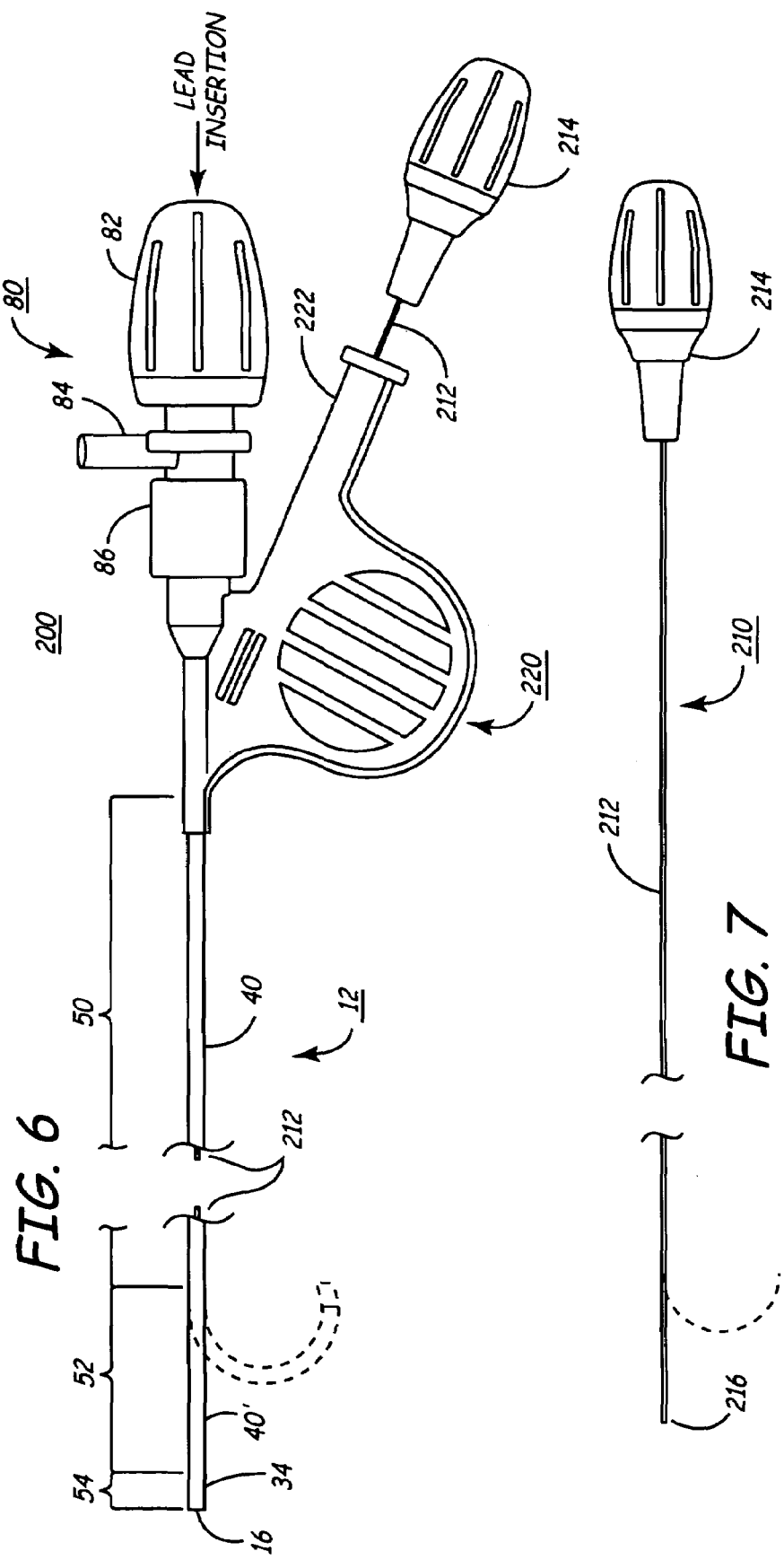

MULTI-LUMEN STEERABLE CATHETER

FIELD OF THE INVENTION

The present invention relates generally to elongated medical devices adapted to be inserted through an access pathway into a body vessel, organ or cavity to locate a therapeutic or diagnostic distal segment of the elongated medical device into alignment with an anatomic feature of interest, and particularly to a catheter, e.g., a multi-lumen steerable catheter having at least one lumen liner formed of a no yield elastomer, particularly such a catheter adapted to be advanced through a tortuous pathway.

BACKGROUND OF THE INVENTION

Many elongated medical devices are known that are inserted through an access pathway into a body vessel, organ or cavity to locate a therapeutic or diagnostic distal segment of the elongated medical device into alignment with an anatomic feature of interest. For example, catheters, introducers and guide sheaths of various types, drainage tubes, and cannulas are available that extend from outside the body through an access pathway to a site of interest and provide a lumen through which fluids, materials, or other elongated medical devices are introduced to the site or body fluids are drained or sampled from the site. Other elongated medical devices include many forms of medical electrical leads that bear sensing and/or electrical stimulation electrodes for sensing electrical signals of the body and/or applying electrical stimulation to the body, e.g. leads for pacing, cardioversion, nerve stimulation, muscle stimulation, spinal column stimulation, deep brain stimulation, etc. Other medical electrical leads bearing physiologic sensors for measuring pressure, temperature, pH, etc, in a distal segment thereof that are adapted to be placed at a site of interest are also known. Other elongated medical devices include guide wires that are directed through tortuous vascular pathways to locate a distal segment thereof typically within a blood vessel. A catheter, e.g. a PTCA balloon catheter for dilating constrictions in blood vessels or delivering stents and grafts or a medical electrical lead having a through-lumen are then advanced over-the-wire to the site. Further elongated medical devices include stiffening stylets that are placed into the lumens of medical electrical leads and in certain guide wires to impart column strength and stiffness to the assembly to enable its transvenous advancement into a heart chamber or cardiac blood vessel.

Such elongated medical devices must have flexibility to navigate the twists and turns of the access pathway, sufficient column strength in the proximal segment thereof to be pushed through the access pathway alone or over a guide wire or through a lumen, and the capability of orienting the distal segment and any electrodes or sensors or ports of the distal segment in a preferred alignment with an anatomical feature at the accessed site so that a diagnostic or therapeutic procedure can be completed. In general terms, the elongated medical device body must also resist kinking and be capable of being advanced through access pathways that twist and turn, sometimes abruptly at acute angles.

It is commonly the practice with certain guide catheters and diagnostic catheters to provide preformed bends at the junctions between segments or pre-curved or shaped segments that are adapted to orient the distal segment and possibly intermediate segments into alignment with an anatomical feature at the accessed site. For instance, many diagnostic procedures involve placing a catheter tip into or a side port across a vascular orifice to inject radiographic fluid through the catheter lumen into the vessel. Such diagnostic catheters have historically been formed of thermoplastic materials that can be heated as in heated water and bent into a shape that the physician can use in attempting to access the vessel opening. A considerable variety of preformed shapes of such catheters have been developed over the years and made available for use in such procedures. Still, the physician may find that the anatomy of any given patient may require altering the bend by heating the catheter, changing the bend and letting it cool before it is advanced to the site where it must make an abrupt change in direction.

The distal segment of a catheter that facilitates the delivery of other medical devices, fluids, drugs, diagnostic agents, or the like, through tortuous pathways of the body frequently needs to be selectively deflected or bent and straightened again while being advanced within the patient to steer the catheter distal end into a desired body lumen or heart chamber or branching blood vessel. Such selective deflection is accomplished by advancing the guide catheter over a previously placed guide wire via a guide wire lumen or by insertion of removable stiffening stylets shaped to impart a selected bend in the distal segment into a stylet lumen or by a steerable mechanism permanently built into the catheter body. Such catheters are referred to herein collectively as "steerable catheters" employing "deflection mechanisms" regardless of use.

For example, commonly assigned U.S. Pat. Nos. 6,280,433 and 6,379,346 disclose steerable catheters that are employed to access the a blood vessel through a percutaneous incision and to be advanced to a site within the vascular system or a heart chamber. A bitumen catheter body is disclosed that comprises a relatively large diameter delivery lumen and a smaller diameter stylet lumen that is blocked at its distal end. The deflection mechanism in this case comprises a stiffening stylet that can be selectively introduced into and removed from the stylet lumen from a proximal hub or handle. The stiffening stylet is advanced distally until the stylet distal end abuts the stylet lumen end to stiffen the catheter body to aid its introduction and advancement. The stylet distal end can be shaped when outside the stylet lumen opening to impart a curve to the catheter body when inserted into the lumen to assist in steering the catheter distal end through the pathway. The stylet lumen is preferably lined with a wire coil sheath, and the handle and delivery lumen are preferably splittable to aid in removing the introducer catheter from an electrical medical lead introduced through the delivery lumen.

Guide wires introduced through the vasculature to access a remote site in a blood vessel or heart chamber or the like constitute a removable form of deflection mechanism to guide introduction of a steerable catheter over-the-wire to locate catheter body distal end at the remote site. A multi-lumen steerable catheter adapted to be introduced through the vasculature over an earlier introduced, small diameter guide wire is disclosed, for example, in U.S. Pat. No. 6,004,310. A small diameter guide wire lumen and larger diameter delivery lumen extend side-by-side through the length of the catheter body. The small diameter guide wire lumen is also surrounded by and reinforced with a wire braid tube or a coiled wire.

One form of a deflection mechanism built into the catheter body to selectively induce a bend in a distal segment or segments comprises the use of heat activated shape memory alloy members that are built into deflection lumens of a steerable catheter distal segment and that change shape to induce or release bends in the catheter body distal segment depending upon their temperature. The shape memory alloy members can be selectively resistance heated to a temperature above body temperature as disclosed in U.S. Pat. No. 4,776,844, for example, to induce a bend in the distal segment of the steerable catheter.

Another form of a deflection mechanism built into the catheter body comprises the use of a deflection mechanism, referred to as control lines or reins or deflection wires or push-pull wires or pull wires (herein "pull wires"), extending between a proximal handle through proximal and distal segments of the catheter body to a point of attachment of the pull wire distal end to the distal segment. The deflection mechanism is manipulated to selectively deflect or straighten the distal segment and, in some cases, intermediate segments of the catheter body. More complex steerable catheters have two or more pull wire lumens and pull wires extending from the handle through the pull wire lumens to different points along the length or about the circumference of the catheter body to induce bends in multiple segments of the catheter body and/or in different directions. In addition, even more complex steerable catheters are known that incorporate one or more distal electrode or sensor and corresponding conductor or inflatable balloons or other components.

For example, many versions of electrophysiology (EP) catheters have been disclosed that are designed to perform mapping and/or ablation of cardiac tissue to diagnose and treat abnormal tissue that induces or sustains cardiac arrhythmias and that employ deflectable distal and intermediate segments controlled by push-pull or pull wire mechanisms. During an EP ablation or mapping procedure, the steerable distal end of the steerable catheter is used to orient the distal tip of the EP device with respect to tissue, such as a patient's endocardium, to facilitate mapping and/or proper delivery of the device's RF or laser energy to the tissue. Highly complex shapes are sometimes found necessary to encircle a pulmonary vein orifice, for example, to ablate the left atrial wall tissue to interrupt arrhythmic pathways. For example, commonly assigned U.S. Pat. Nos. 5,445,148, 5,545,200, 5,487,757, 5,823,955, and 6,002,955 disclose a variety of such shapes and mechanisms for forming the shapes.

In most simple or complex steerable catheters incorporating pull wire(s), a relatively large diameter delivery lumen and relatively small diameter pull wire lumen(s) (as well as other lumens for conductors or the like) are desirable. At the same time, the outer diameter of the steerable catheter must be minimized so that it can be readily advanced within the patient. Exemplary multi-lumen and bitumen steerable catheters having relatively larger delivery lumens and incorporating pull wires in relatively small pull wire lumens extending alongside the delivery lumens to selectively deflect the distal segment of the catheter are disclosed in U.S. Pat. Nos. 2,688,329, 3,605,725, 4,586,923, 5,030,204, 5,431,168, 5,484,407, 5,571,085, 6,217,549, 6,251,092, and 6,371,476, and in published U.S. Patent Appln. Pub. No. 2001/0049491. Many of these exemplary steerable catheters are relatively simple, having only a single pull wire lumen and a delivery lumen extending between proximal and distal lumen end openings for introduction or withdrawal of fluids, or delivery of drugs or other medical devices into the body.

The walls of multi-lumen steerable catheters are necessarily thin in order to maximize the size of the delivery lumen and minimize the outer diameter of the steerable catheter and strong to exhibit column strength and pushability. Consequently, a tubular reinforcement or a metal wire braid reinforcement is employed within at least a proximal segment of the outer wall or sheath of the typical steerable catheter body to stiffen the thin catheter wall as disclosed in many of the above-referenced patents and in commonly assigned U.S. Pat. Nos. 5,738,742 and 5,964,971. The reinforced catheter wall enables torque transmission to the catheter distal end as the proximal end of the catheter outside the patient is rotated.

In the fabrication of such steerable catheters, it is necessary to extend the pull wire from a distal point of attachment proximally through the pull wire lumen extending through the deflectable distal segment and the non-deflectable proximal segment of the catheter body to an exit point so that the pull wire proximal end can be coupled to a steering mechanism of the handle. The proximal ends of the pull wires of such steerable catheters either exit through the side wall of the catheter body at a point distal to the catheter body proximal end, as shown in the above-referenced '030 patent and '49491 application, or from a more proximal end opening of the catheter body and are attached to a handle to be manipulated in use to induce a bend or to straighten the deflectable distal segment of the catheter body. Thus, the handle usually encloses the portion of the catheter body where the proximal end of the pull wire is exposed, and the pull wire proximal end is attached to a pull wire knob or ring that can be manipulated by the user to induce a deflection in the catheter body distal segment to steer it.

The relatively smaller diameter pull wire lumen(s) is typically formed to extend alongside the large diameter delivery lumen, such that both the delivery lumen and pull wire lumen are off-axis from the longitudinal axis of the catheter body when fabrication is completed. In the above-referenced '092 patent, the pull wire lumen is formed within an inner polymeric core contained within the outer sheath wall alongside the delivery lumen. The pull wire distal end is attached to the catheter distal end by a ring that encircles the delivery lumen liner and is embedded in a soft tip of the catheter body. In the above-referenced '4941 publication, the pull wire lumen is formed when the outer sheath wall is formed over and embedding the wire braid and delivery lumen. In the above-referenced '407 and '085 patents, at least the proximal, non-deflectable, segment of the pull wire lumen is lined by a tubular thin-walled metal or plastic sheath. In the above-referenced '168, '476 and '549 patents, the pull wire lumen is defined by the lumen of a coiled wire or wire braid tubing. It is suggested in the '549 patent, referring to FIGS. 24A and 24B, that the coiled wire can be included within a plastic sleeve or liner.

Many approaches to the fabrication of the large diameter delivery lumen and the small diameter pull wire lumens within the wire reinforced outer sheath have been disclosed. The large diameter delivery lumen is typically defined by a delivery lumen liner formed of an elastic material, e.g. PTFE fluoropolymer tubing, as described, for example, in the above-referenced '49491 publication and '092 patent. Typically, reinforced steerable catheter bodies are formed employing a thin wall, PTFE liner to define the delivery lumen, because PTFE is relatively lubricious and crush resistant so that a relatively circular, large diameter, thin wall PTFE liner can provide a large diameter delivery lumen. The PTFE wall surface of a PTFE liner has a very low coefficient of friction when leads, guidewires or other catheters are passed through it particularly through curves in the lumen where contact stresses against the wall surface are greatest. In addition, PTFE has a higher melt temperature than the other thermoplastic polymers used in the catheter construction, which allows thermal reflow processes to be used to reflow other polymers over the PTFE liner. PTFE has a middle durometer that is not too stiff in the distal segments but not too soft in the proximal segments, thus making it suitable to traverse the length of the catheter shaft. While PTFE tubing enjoys these advantages, the use of PTFE tubing in the catheter body distal segment renders the distal segment relatively stiff and difficult to form into a bend employing a pull wire or stylet as described above or to track short radius turns of a guide wire.

Due to PTFE surface characteristics, it is also difficult to bond thermoplastic materials embedding wire braid to the PTFE tubing unless the tubing surface is etched. The above-referenced '092 patent discloses the concepts of terminating the wire braid proximal to the catheter body distal end and molding a softer durometer distal end segment to the catheter body distal end to the distal end of the PTFE delivery lumen liner. This approach further complicates the fabrication process.

In thin wall catheters, the outer jackets on the distal segments rarely go below Shore 35D durometer or flexural modulus of 2000 psi. The stainless steel braid wire used in catheters has tended to go up in temper, effectively increasing how sharp of a bend or how much of a loading is sustained without yielding the wire and kinking/buckling the catheter shaft. The braid wire is not usually the limiting factor in atraumatic tip designs although material condition, wire diameter, number of wires, and braid angle have to be optimized. The stiffness of the PTFE liner within the distal segment constitutes the limiting factor in achieving a highly bendable distal end segment. However, a lumen liner is needed in the distal segment to maintain the integrity of each such lumen. Moreover, the distal segment cannot be made too soft as tip control and feel are then lost.

Consequently, a need remains for a steerable catheter body having a relatively flexible and soft distal segment with a large diameter, crush resistant, delivery lumen that is simple to fabricate and reliable in use. A need remains for a catheter body having a soft distal segment and tip that is less traumatic than current technology while still capable of transmitting enough force and torque to effectively negotiate the catheter to the desired anatomical location.

The design of such steerable catheters must be highly robust to ensure the integrity of the delivery lumen, the reliability of use of the pull wire, and to provide the desired degree of deflection. The fabrication of such bitumen steerable catheter bodies is therefore highly labor intensive and time consuming to consistently achieve these design objectives. Simplification of the fabrication steps and the reduction of assembly time without compromising design objectives remains a desirable goal. The present invention satisfies these and other needs.

SUMMARY OF THE INVENTION

A first aspect of the present invention is directed to an elongated catheter for introduction into a patient's body comprising a catheter hub and an elongated catheter body extending from a catheter body proximal end coupled with the catheter hub and a catheter body distal end, a catheter body axis, a catheter lumen extending from the catheter hub to the catheter body distal end. In accordance with the present invention, a lumen liner is formed of a "no yield" elastomer, and the distal segment of the lumen liner and other components of the catheter body are embedded within a catheter body sheath formed of a very low flexural modulus thermoplastic material. The tubular lumen liner formed of a no yield elastomer exhibits no definite yield point when it is stretched axially.

A further aspect of the present invention is directed to an elongated steerable catheter for introduction into a patient's body comprising a steerable catheter hub and an elongated catheter body extending from a catheter body proximal end coupled with the hub and a catheter body distal end, a catheter body axis, a delivery lumen extending from the hub to the catheter body distal end and a deflection lumen adapted to receive a deflection mechanism operable from the catheter body proximal end to selectively impart a bend in a distal segment of the catheter body.

In accordance with this aspect of the present invention, the delivery lumen liner is formed of a no yield elastomer, and the distal segment of the delivery lumen liner and other components of the catheter body are embedded within a catheter body sheath formed of a very low flexural modulus thermoplastic material. The tubular delivery lumen liner formed of a no yield elastomer exhibits no definite yield point when it is stretched axially.

The deflection mechanism and respective deflection lumen preferably comprises one of: (1) a stylet adapted to be advanced in a stylet lumen into abutment with the stylet lumen distal end within the catheter body; (2) a pull wire extending from the hub through a pull wire lumen to a distal attachment point within the catheter body; (3) a guide wire adapted to be received in a guide wire lumen extending from the hub to a guide wire lumen distal end opening; and (4) a shape memory alloy member within an auxiliary lumen in the distal catheter body segment adapted to change shape upon an induced temperature change.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other features and advantages of the invention will become apparent from the following description in which the preferred embodiments are disclosed in detail in conjunction with the accompanying drawings in which:

FIG. 3 is a plan view of a pull wire operated steerable catheter formed of the catheter body of FIGS. 1 and 2 and a universal hub;

FIG. 4 is a plan view of the pull wire employed in the pull wire operated steerable catheter of FIG. 3;

FIG. 6 is a plan view of a stylet operated steerable catheter formed of the catheter body of FIGS. 1 and 2 and a universal hub;

FIG. 7 is a plan view of the removable stylet employed in the stylet operated steerable catheter of FIG. 6;

DETAILED DESCRIPTION OF THE PREFERRED EMBODIMENTS

The present invention may be implemented in a wide variety of elongated medical devices to facilitate advancement of the device distal end or distal section through constricted and twisting access pathways, including the vascular system, of the body and/or to alignment of the distal section or segments thereof into conformance with an anatomical structure at a site of interest.

The present invention can be implemented in catheters having a single lumen or multiple lumens extending the length of the catheter body. For convenience, the illustrated preferred embodiments depict steerable catheters having at least one delivery lumen and a deflection lumen that can receive a deflection mechanism to induce bends and curves in at least an intermediate segment of the catheter body. Both of the delivery and deflection lumens are defined by lumen liners, and at least one (or both) of the lumen liners is formed of a no yield elastomer.

Figure 1:
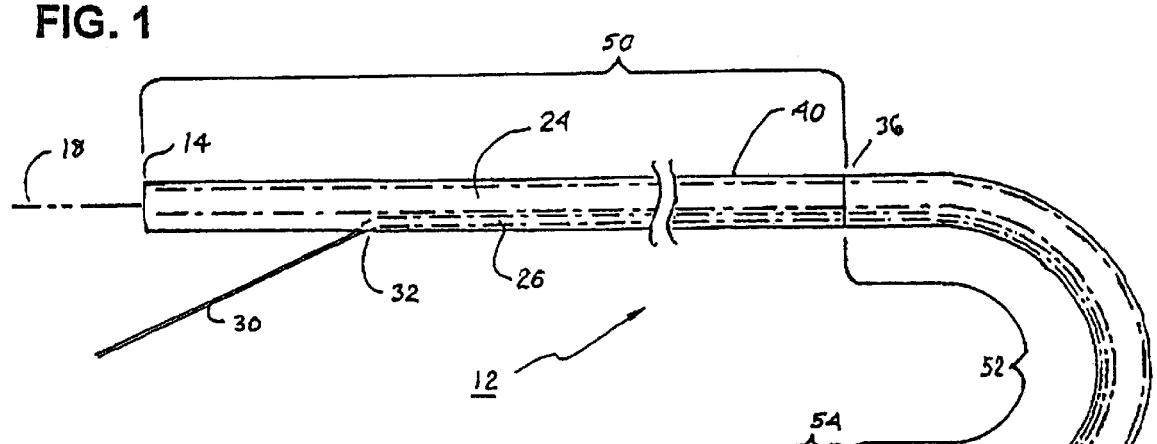
FIG. 1 is a plan view of a catheter body that the present invention is advantageously incorporated into.
Figure 2:
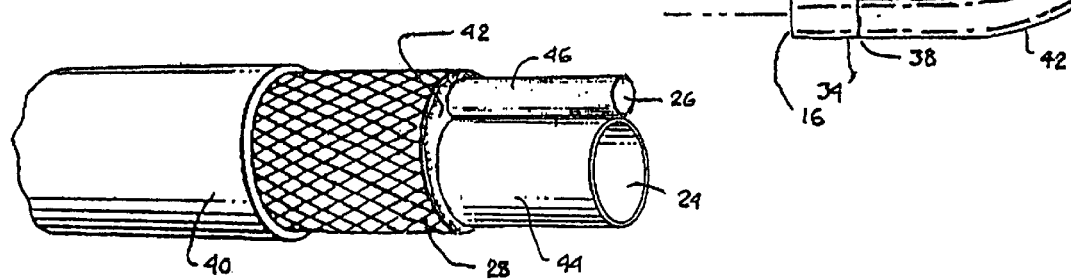
FIG. 2 is a perspective view of a section of the catheter body of FIG. 1 illustrating the internally disposed wire braid overlying the side-by-side aligned deflection lumen and delivery lumen.

Thus, the present invention is described in the context of a steerable catheter, and several embodiments are described herein by way of example. First, a multi-lumen catheter body 12 that may incorporate the concepts of this invention is shown in FIGS. 1 and 2 with a bend induced in the intermediate segment 52 thereof. The elongated catheter body 12 has a catheter axis 18 and extends from a catheter body proximal end 14 adapted to be coupled with a catheter hub to a catheter body distal end 16. A delivery lumen 24 extends through the catheter body 12 from a delivery lumen proximal end opening at the catheter body proximal end 14 to a delivery lumen distal end opening at the catheter body distal end 16. An "accessory" or deflection lumen 26 extends alongside the delivery lumen 24 through the catheter body 12 from a deflection lumen proximal end opening 32 through sheath 34 to either a deflection lumen closed distal end proximal to the catheter body distal end 16 or a deflection lumen distal end opening at the catheter body distal end 16, depending upon the type of steerable catheter formed with the steerable catheter body 12.

Generally speaking, the catheter body 12 includes a number of segments, e.g., segments 50, 52 and 54, along its length formed of different materials and structural components to provide different handling characteristics. The segments 50 and 52 are formed of respective outer sheath segments 40 and 42 of materials that contribute to making the most proximal segment 50 relatively stiff to impart column strength and torqueability and to making intermediate segment 52 more flexible and bendable upon manipulation of the deflection mechanism. The distal segment 54 incorporates a soft sheath 34 that is intended to be atraumatic at catheter body distal end 16 to avoid injury to tissue as described in the above-referenced '092 patent, for example. Intermediate segment 52 is axially joined to proximal segment 50 at junction 36, and the intermediate segment 52 is joined to distal segment 54 at junction 38. The present invention improves the flexibility of the bendable intermediate segment 52 and the characteristics of the atraumatic distal segment 54 and offers further advantages in fabrication and handling characteristics.

The catheter body 12 can be between about 50 cm and 300 cm in length, but is typically and more preferably between about 100 cm and 150 cm in length. The catheter body 12 is preferably circular or slightly oval or triangular in cross-section and having a maximal outer diameter in the range of 5 French (1.67 mm) to 11 French (1.44 mm). Typically, proximal segment 50 constitutes about 70–90% of the total length of catheter body 12, and relatively more flexible intermediate segment 52 and distal segment 54 constitute the remaining 10%–30% of the length of catheter body 12.

The deflection lumen 26 is adapted to receive a deflection mechanism 30 extended through in the outer sheath side opening 32 operable to selectively impart a bend in the intermediate segment 52 of the catheter body 12. The deflection mechanism 30 shown schematically in FIG. 1 comprises one of a permanently inserted and distally attached pull wire, a removable stylet, a removable guide wire or conductors for applying current to and resistively heating a shape memory alloy strip inserted into the intermediate segment 52. The removable stylet can be a steerable stylet of the types described in commonly assigned U.S. Pat. Nos. 5,873,842 and 6,146,338, for example.

Referring to FIG. 2, the catheter body 12 is formed of a proximal outer sheath segment 40 and an intermediate outer sheath segment 42 encasing a tubular wire braid 28, a delivery lumen liner 44 defining delivery lumen 24, and a deflection lumen liner 46 defining the deflection lumen 26. The delivery and deflection lumen liners 44 and 46 may have a substantially uniform cross-sectional area along the lengths thereof or may vary along the lengths thereof. It is desirable for the catheter body 12 to be constructed to assure that the delivery and deflection lumens 24 and 26 maintain their cross-sectional shape and to provide the desired flexibility, pushability, torqueability and low profile of the catheter body 12 required for its intended use in a steerable catheter. It is further desirable that the inner surfaces of the lumen liners 44 and 46 are lubricious to enable free passage or movement of devices therethrough. It is also desirable that the lumen liners 44 and 46 resist rupture or penetration.

The tubular wire braid 28 may be of a variety of different materials and configurations designed to impart the desired stiffness to the catheter shaft section and in particular ensure that the cross-sectional shape of the delivery and deflection lumen liners 44 and 46 to remain substantially undistorted as the catheter body 12 undergoes high flexure encountered traversing sharp bends in the vascular pathway. The wire braid 28 constructions include metallic and non-metallic fibers or wires or ribbons that may be configured in a single or multiple spirals, braids or knits as is known in the art. Wire braid 28 can be formed of a metallic material, such as a super-elastic alloy or stainless steel, or non-metallic materials such as those made of polyaramids, carbon fibers, Dacron, Nylon, or liquid crystal polymer and can even be made using natural fibers such as silk and cotton.

The braid characteristics, such as pick, angle, spacing, the nature of the strand (i.e., flat or round), and the like, can be selected together with the characteristics of the thermoplastic proximal and intermediate outer sheath segments 40 and 42 to provide a desired torsional stiffness and axial flexibility of the proximal and bendable intermediate segments 50 and 52, respectively. In an exemplary embodiment, the wire braid is 304 LV stainless steel formed from 0.002 inches to 0.003 inches diameter round strands at a 60°–65° braid angle. The reinforcing and stiffening properties of the wire braid 28 allows the delivery lumen liner 44 and the deflection lumen liner 46 to be formed of thin wall tubing maximizing lumen diameter and yet maintaining the integrity of the lumen cross-sectional shape.

The outer sheath segments 40 and 42 may be made from any suitable, biologically compatible, thermoplastic polymer, e.g., nylon, polyether block copolymers (e.g., Pebax®), polyolefins (e.g., Hytrel®, DuPont, Wilmington, Del.), and the like, can be employed, although a polyurethane, e.g., Pellethane 2363, typically having a hardness in the range from about 35D to 75D, is preferred. Other possible polymers include polyethylene, polypropylene, polystyrene, polyethylene terephthalate, polyesters, polyvinyl chloride, silicone and lubricious polymers such as polyfluorocarbons or polysulfones. During fabrication, the outer sheath segment 40 in proximal segment 50 and outer sheath segment 42 in intermediate segment 52 are heated to flow through the interstices of the wire braid 28 and about the outer surfaces of the delivery lumen liner 44 and the deflection lumen liner 46 as shown in FIG. 2 and described further below.

In a preferred embodiment, the distal sheath 34 is formed of Tecoflex® EG80A B20 polyether block copolymers supplied by Thermedics Polymer Products, Woburn, Mass. The proximal outer sheath segment 40 is formed preferably of one or more of Pebax® 7033 SA-00, Pebax® 7033 SA-01, Pebax® 7033 SN-00, Pebax® 7033 SN-01 polyether block copolymers, all supplied by Atofina Chemicals, Inc., Philadelphia, Pa. Transition sections between outer sheath segments can be formed of Pebax® 6333 SA-00, Pebax® 6333 SA-01, Pebax® 6333 SN-00, Pebax® 6333 SN-01, Pebax® 5533 SA-00, Pebax® 5533 SA-01, Pebax® 5533 SN-00, Pebax® 5533 SN-01, Pebax® 4033 SA-00, Pebax® 4033 SA-01, Pebax® 4033 SN-00, Pebax® 4033 SN-01 polyether block copolymers. Pellethane 2363 series or Tecothane polyurethanes could be used in a similar fashion. Tecothane polyurethanes are made by Thermedics Polymer Products, Woburn, Mass. Pellethane® polyurethanes are made by The Dow Chemical Company, Midland Mich. sheath segment 40

The deflection lumen liner 46 preferably comprises a relatively thin wall tube formed of a durable material having a low coefficient of friction to minimize the magnitude of force required to insert or axially move a deflection mechanism 30 within the deflection lumen 26. The deflection lumen liner 46 is not necessarily made of a lubricious material. A lubricant can be used on the stylet or guidewire traversing the deflection lumen as is done with pacing leads. Or a lubricant can be coated onto the inside surface of the deflection lumen liner 46. For reflow manufacturing processes, the material forming the deflection liner 46 should have a higher melt temperature than the outer sheath materials that are reflowed around it. Suitable polymers for use in forming the deflection lumen liner 46 includes polyurethane, high density polyethylene (HDPE), low density polyethylene (LDPE), polyvinylchloride (PVC), fluoropolymers including PTFE, FEP, vinylidene fluoride, and their mixtures, polyimides. Most preferably, deflection lumen liner 46 is made from thin-wall polyimide tube, having a wall thickness of 0.0005 inches (0.013 mm) to 0.0010 inches (0.025 mm). The lumen diameter and wall thickness of the deflection lumen liner 46 and its specific properties may depend in part upon the diameter and type of deflection mechanism 30 intended to be inserted into the deflection lumen 26 and the requisite clearance to assure smooth movement of a movable deflection mechanism.

The delivery lumen liner 44 is constructed from a "no yield" elastomer that exhibits no definite yield point when the lumen liner is stretched axially as determined by ASTM D638 under dry test conditions. On a stress-strain diagram, the yield point of is usually denoted as a point of increasing strain without an increase in stress associated with it. For example, a 0.2% offset is used where the initial slope of the stress-strain curve is plotted starting at 2% strain and zero stress. When the actual curve crosses this offset line, that is the arbitrary yield point. A no yield elastomer does not exhibit any yield point or exhibits a yield point at such a stress as would not be encountered in the application in question.

The use of a no yield elastomer to form the delivery lumen liner 44 allows for sharper bends to be induced in the catheter body 12 with higher localized strain rates than associated with current guide catheter and diagnostic catheter technology. Moreover, the no-yield elastomer delivery tube is more forgiving when it is subjected to localized stresses due to bending of the wire braid 28. Consider the diamond-shaped void space between the braid wires making up the wire braid 28. When the catheter body is bent, the wires are pivoting to create a high localized strain at the corners of the diamond-shaped void space (commonly referred to as the pic crossings). The strain is highly geometry dependent, but a no yield or high yielding material allows more pivoting of the wires without yielding or pulling away or initiating failure of the catheter body 12. A no yield elastomer of the types described herein could also be used to form the deflection lumen liner 46.

The preferred no yield elastomer is EMS Chemie Grilamid® ELY 2702 elastomer, which exhibits a 51D Shore durometer and a flexural modulus of 25 ksi, 25,000 psi. By contrast, PTFE tubing material exhibits a 50D–65D Shore durometer and a flexural modulus of 27 ksi, and Pebax® tubing material exhibits a 70D Shore durometer and a flexural modulus of 67 ksi. Such an elastomer is similar to PTFE in hardness and in flexure but possesses a higher material yield point that is advantageous when the catheter body 12 is in high flexure (bending) as described above. Similarly, the 70D Pebax® tubing material used for liners of the Vector™, Zuma™ and 72™ guide catheters sold by Medtronic AVE does not perform as well in high flexure.

According to the present invention, the elastomer is roughly the same durometer and flexural modulus as PTFE. A delivery lumen liner 44 formed of the elastomer exhibits no defined yield point, unlike a delivery lumen liner 44 formed of the PTFE. A delivery lumen liner 44 formed of the elastomer can be formed into sharp curves and bends as it stretches without yield failure. In other words, The elastomer is a somewhat unique thermoplastic polymer in the sense that it keeps stretching without yielding, i.e., the tubing returns to its original length and shape when the force applied to stretch and bend it is removed.

According to the present invention, the elastomer is not lubricious like PTFE, so a hydrophilic (water shedding) coating of the liner lumen surface is necessary. The hydrophilic coating lowers the lumen surface coefficient of friction to nearly zero, making it easier to pass a given device through the hydrophilic coated elastomer than through a PTFE liner lumen.

The materials identified above that are reflow molded through the wire braid 28 and against the delivery lumen liners 44 and 46 to form the outer sheaths 40 and 42 and the distal sheath 34 advantageously bond well with elastomer. Therefore, it is not necessary to chemically surface etch the outer surface of the delivery lumen liner 44 at least in the distal segment 54 formed of the elastomer as is the case when the delivery lumen liner 44 is formed of PTFE to adhere the distal sheath 34 to it.

The cost of the delivery lumen liner 44 formed of the elastomer with the hydrophilic coating applied to the lumen inner surface is about the same as the cost of the delivery lumen liner 44 formed of a surface etched PTFE tubing.

In one embodiment, the elastomer is extruded to about 0.002 inches (0.051 mm) to 0.003 inches (0.078 mm) wall thickness. The extruded tubing is drawn down onto a PTFE-coated mandrel having a diameter defining the delivery lumen diameter to form the resulting final wall thickness of about 0.0015 inches (0.039 mm) to 0.002 inches (0.051 mm). The delivery lumen liner inner diameter ranges from about 0.072 inches (1.83 mm) to about 0.086 inches (2.18 mm) depending upon the intended use of the resulting catheter shaft 12.

As noted above, the inner lumen surfaces of the delivery lumen liner 44 and the deflection lumen liner 46 are preferably coated to increase lubricity with a lubricant, preferably a hydrophilic polyacrylamide. The polyacrylamide coating is preferably applied to the lumen surface by dipping or spraying or the like.

In fabrication, mandrels are inserted into the coated delivery lumen liner 44 and the coated deflection lumen liner 46 to prevent their collapse. The mandrel supported delivery lumen liner 44 and deflection lumen liner 46 are aligned longitudinally in side-by-side relation. The stainless steel braid wire with a double or triple spring temper is braided directly over the aligned delivery lumen liner 44 and the deflection lumen liner 46. Or the wire is braided into a wire braid tube, and the delivery lumen liner 44 and the deflection lumen liner 46 are inserted into the wire braid tube and tied down at the ends.

The thermoplastic outer sheath segments 40, 42 are formed over the wire braid 28 by placing pre-formed tubes of the thermoplastic materials forming outer sheath segments 40, 42 over the wire braid 28 and the mandrel supported delivery lumen liner 46 and deflection lumen liner 44 and then heating the assembly so that the thermoplastic material impregnates the wire braid 28 to form a unitary structure. A length of heat shrink tubing is fitted over the assembly, the tubing is shrunk over the assembly by application of heat, and the assembly is subjected to heat to melt the thermoplastic material into the wire braid 28 and around the delivery lumen liner 44 and deflection lumen liner 46. The assembly is cooled, the heat shrink tubing is removed, and the wire mandrels are withdrawn from the delivery lumen 24 and deflection lumen 26.

A distal section of the wire braid 28 is typically left exposed to be embedded within the distal sheath 34. The exposed wire braid wire ends can be trapped from unraveling by being embedded within a very short length of a rigid nylon (ASTM D790 flexural modulus>120,000 psi) or Atofina PEBAX® 7033 SA-00 or 7233 SA-00 nylon copolymer (ASTM D790 flexural modulus of 109,000 psi). This embedding material is selectively reflowed into the wire braid 28 to anchor and terminate the high temper wire braid 28 into a polymer with a higher softening temperature so the fused wire ends can be trimmed so that wires do not uncross or unduly stiffen the distal segment 52. The deflection lumen liner 46 is either left in place or trimmed back to the wire braid 28 and further processed as described in reference to the particular steerable catheter embodiments.

The delivery lumen liner 46 and other components of the distal segment 54 are then embedded within a catheter body distal sheath 34 formed of a very low flexural modulus thermoplastic material (ASTM D790 flexural modulus≦1,300 psi) in the distal segment 54. As noted above, a preferred thermoplastic material comprises Thermedics Tecoflex® 80A B20 aliphatic polyurethane since it softens in the patient's body more than other urethanes or other polymers of about the same durometer. The catheter body distal sheath 34 is fitted over the distal segment of the delivery lumen liner 44 and deflection lumen liner 46. An FEP heat shrink tube is advanced over the sheath 34, and the sheath 34 is fused into the braid and against the delivery lumen liner 44 and deflection lumen liner 46. A tube oven with an iris is used because the softening temperature of the Themedics Tecoflex® 80A B20 substantially lower than the rest of the material. The distal sheath 34 extends out of the oven and is heated in a separate operation at a lower temperature.

A variety of transition materials can be used near the distal end between the intermediate sheath segment 42 and the distal sheath 34 such as Atofina Pebax® 6333 SA-00, 5533 SA-00, 4033 SA-00 or EMS Chemie Grilamid® ELY 60 or ELY 2702 (50,000 psi>ASTM D790 flexural modulus>10,000 psi).

Specific Steerable Catheter Embodiments

The catheter body 12 formed of these materials can be incorporated into a variety of steerable catheters. Specific steerable catheters 100, 200, 300 and 400 that are useful to traverse tortuous pathways through a skin incision in a patient's body to access a remote implantation site for implanting an electrical medical lead, e.g., a cardiac lead, are depicted in FIGS. 3–12.

These illustrative steerable catheters 100, 200, 300 and 400 are particularly useful in introducing small diameter cardiac leads that are devoid of a stylet lumen and are so flexible and possess such low column strength, pushability and torqueability that the lead distal end cannot be advanced transvenously and positioned at the desired implantation site without assistance. Moreover, one particular use of these illustrative steerable catheters 100, 200, 300, 400 is to introduce such cardiac leads that are formed using stranded wire conductor(s) within a lead body diameter of about 1 to 3 French (0.010 inches to 0.026 inches or 0.025 mm to 0.069 mm). The lead body outer diameter is minimized by use of such conductors and by eliminating the lumen for receiving a stiffening stylet. However, the illustrative steerable catheters can also be employed to introduce cardiac leads that employ coiled wire conductors with or without a lumen for receiving a stiffening stylet. In the latter case, the stiffening stylet need not be used to achieve the introduction.

Figure 13:
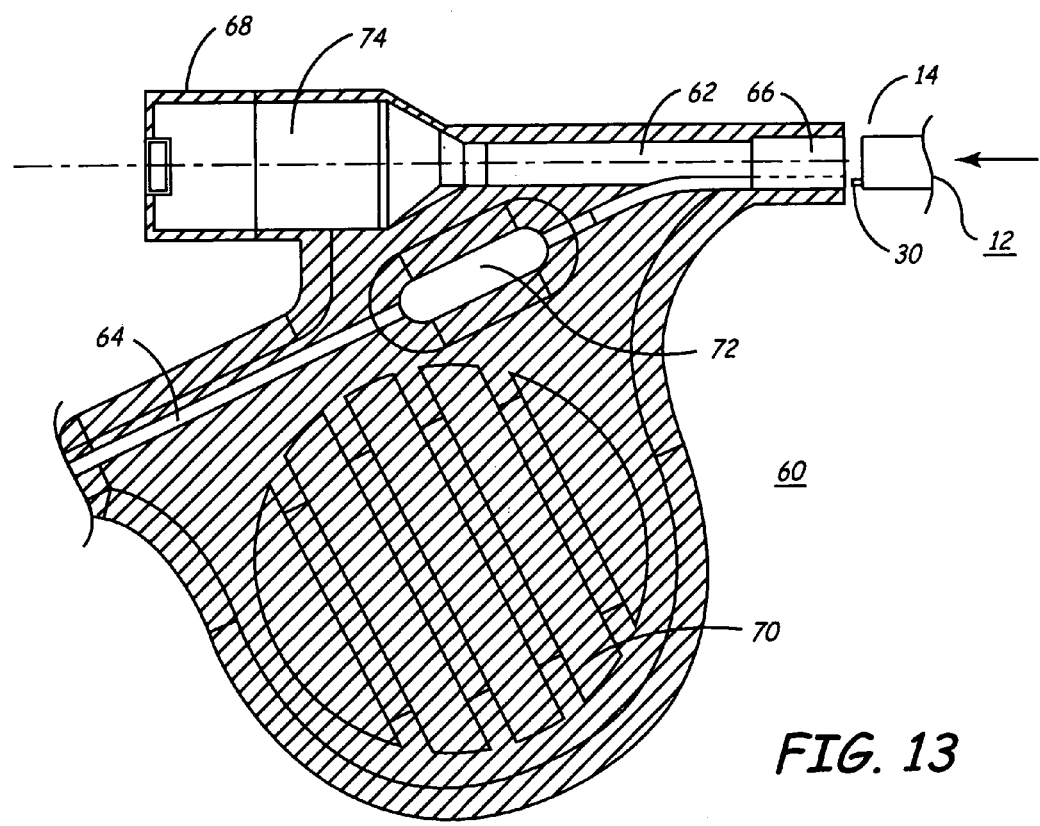
FIG. 13 is a partial cross-section view of the universal hub body illustrating the internal passages to the catheter body delivery lumen and deflection lumen

Each of the steerable catheters 100, 200, 300 and, 400 comprises a catheter body 12 and deflection mechanism 30 of FIG. 1 attached at catheter body proximal end 14 to a hub body 60 of hubs 120, 220, 320 and 280 depicted in FIGS. 3, 6, 9 and 11, respectively. The common hub body 60 shown in cross-section in FIG. 13 is modified somewhat to accommodate the particular deflection mechanism of the steerable catheters 100, 200, 300, 400. The hub body 60 comprises a hub delivery lumen 62 and a hub deflection lumen 64 branching apart from one another where the catheter body proximal end 14 is received within an enlarged common hub lumen 66. The catheter body proximal end 14 is inserted into the common hub lumen 66 so that the deflection lumen 26 and the deflection mechanism 30 therein are aligned axially with the hub deflection lumen 64 and the catheter body delivery lumen 24 is aligned axially with the hub delivery lumen 62.

An enlarged, relatively flat paddle 70 is formed extending away from the hub delivery lumen 62 and a hub deflection lumen 64 that can be gripped on either side by the fingers to assist in holding and manipulating the hubs 120, 220, 320, 280 during adjustment of the deflection mechanism 30 and advancement of the catheter body 12 through the tortuous pathway. A window 72 is formed through the hub body 60 across the hub deflection lumen 64 so that a portion of the deflection mechanism 30 can be seen in the window 72.

The hubs 120, 220, 320 and 280 depicted in FIGS. 3, 6, 9 and 11, respectively, also comprise a hemostasis valve 80 that provides a lead insertion lumen axially aligned with the hub delivery lumen 62 so that a cardiac lead of the types described above can be inserted therethrough and into the catheter body delivery lumen 24. The hemostasis valve 80 comprises a proximal rotating closure knob 82, an intermediate side port 84 for attachment to an extension hose and stopcock (not shown), and a distal rotating locking collar 86 for securing a valve to a luer hub fitting 86. The knob 82, side port 84, and collar 86 constitute a standard hemostasis valve 80 to introduce or aspirate fluids into or from the delivery lumen or to enable insertion of a cardiac lead or other implantable or diagnostic elongated medical device into the delivery lumen.

The hub body 60 of 120, 220, 320 and 420 is preferably molded of Grilamid® ELY-2702. The hub body can be molded to the proximal ends of the catheter bodies.

Pull Wire Catheter Embodiment

Figure 5:
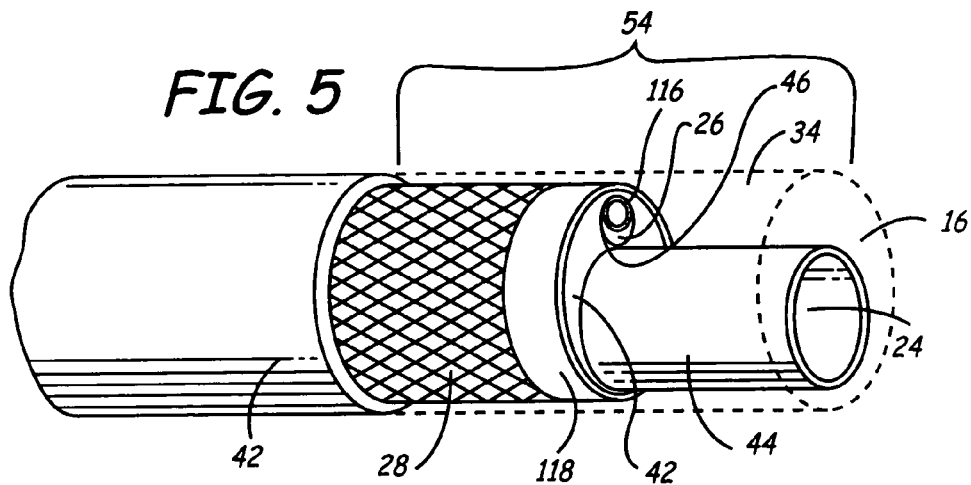
FIG. 5 is a perspective view of the distal segment of the catheter body of FIG. 3 illustrating the fixation of the pull wire to the internally disposed wire braid overlying the side-by-side aligned deflection lumen and delivery lumen proximal to the catheter body distal end.

The steerable catheter 100 illustrated in FIG. 3 comprises the catheter body 12 modified at the catheter body distal end 16 as depicted in FIG. 5 and attached at the catheter body proximal end 14 to a universal hub 120. Universal hub 120 is formed of hub body 60 depicted in cross-section in FIG. 13 and described above, modified by the depicted elongated side port extension 122 and incorporating the hemostasis valve 80. The deflection mechanism 30 of the steerable catheter 100 illustrated in FIG. 3 comprises a pull wire 110 in this embodiment that is separately depicted in FIG. 4. The pull wire 110 is inserted through the hub deflection lumen 64 and the catheter body deflection lumen 26 that collectively comprise a pull wire lumen and is affixed at the pull wire lumen distal end to the catheter body 12 in a manner depicted in FIG. 5. The catheter body distal segment 54 only comprises a distal segment of the delivery lumen liner 44 and the distal outer sheath 34 (shown in broken lines to illustrate interior components). The deflection lumen liner 46 is truncated proximal to the catheter body distal end 16. The distal outer sheath 34 is reflow molded in the distal segment 54 to encase the depicted components to either provide the catheter body distal end 16 having the same diameter as the catheter body 12 along its length as depicted or having a taper to a reduced diameter surrounding the distal end of the delivery lumen liner 44.

The pull wire 110 comprises a length of stainless steel wire 112 extending from a proximal knob 114 coupled to the proximal end of stainless steel wire 112 to a ring 118 welded to the pull wire distal end 116. The wire 112 can have a diameter of about 0.008 inches tapered down to 0.006 inches. The distal segment of the deflection lumen liner 46 is trimmed back to the wire braid 28, and a slit can be formed through the wire braid 28 and the deflection lumen liner 46. Ring 118 is fitted against the wire braid 28 at the formed slit as shown in FIG. 5 and embedded therein during the reflow molding of the above-described embedding material or formation of the distal sheath 34.

In this illustrated fabrication of steerable catheter 100, the stainless steel wire 112 extends from the distal point of attachment proximally through the pull wire lumen 26 extending through the intermediate segment 52 and the non-deflectable proximal segment 50 of the catheter body 12 and then through the hub pull wire lumen 64 within side branch or port 122. The pull wire knob 114 can be pulled away from the side branch or port to induce the bend in the intermediate outer sheath segment 42 depicted in broken lines.

The steerable catheter 100 is advanced through the tortuous pathway until the catheter body distal end 16 is advanced to the implantation site for implantation of a cardiac lead. The cardiac lead is then advanced through the hub delivery lumen 62 and the catheter delivery lumen 24 to eject the cardiac lead distal end at the implantation site where it is fixed in any of the manners known in the art.

In this pull wire embodiment, the catheter body 12 can preferably have an outer diameter of about 0.118 inches (3.0 mm). The delivery lumen diameter is preferably about 0.086 inches (2.18 mm) and the deflection lumen diameter is preferably about 0.013 inches (0.33 mm).

Stylet Guided Steerable Catheter

Figure 8:
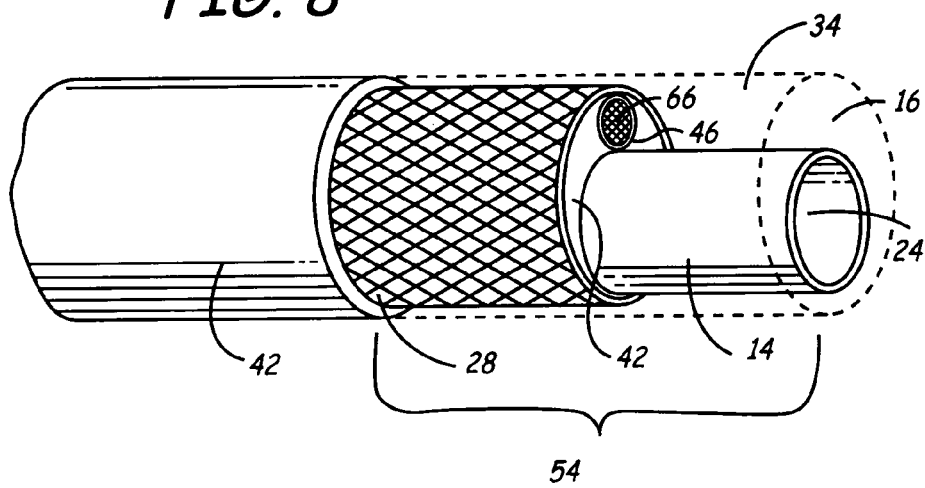
FIG. 8 is a perspective view of the distal segment of the catheter body of FIG. 6 illustrating the blocking of the deflection lumen distal end to inhibit introduction of fluids into the deflection lumen.

The steerable catheter 200 illustrated in FIG. 6 comprises the catheter body 12 modified at the catheter body distal end 16 as depicted in FIG. 8 and attached at the catheter body proximal end 14 to the universal hub 220. Universal hub 220 is formed of hub body 60 depicted in cross-section in FIG. 13 and described above, modified by the depicted elongated side port extension 222 and incorporating the hemostasis valve 80. The deflection mechanism 30 of the steerable catheter 200 illustrated in FIG. 6 comprises a stylet 210 in this embodiment that is separately depicted in FIG. 7.

The stylet 210 comprises a length of stainless steel wire 212 extending from a proximal stylet knob 214 coupled to the proximal end of stainless steel wire 212 to the stylet wire distal end 216. The stylet wire 212 can have a diameter of about 0.022 inches (0.56 mm). The stylet wire 212 can be manually shaped to impart a curve in its distal segment and inserted through the hub deflection lumen 64 and the catheter body deflection lumen 26 that collectively comprise a stylet lumen until the stylet distal end is adjacent or abutted against the closed distal end of the catheter body deflection lumen 26. The curve formed in the stylet wire 212 is imparted to the catheter body intermediate segment as shown in broken lines in FIG. 6.

Again, the catheter body distal segment 54 illustrated in FIG. 8 only comprises a distal segment of the delivery lumen liner 44 and the distal outer sheath 34 (shown in broken lines to illustrate interior components). The deflection lumen liner 46 is truncated proximal to the catheter body distal end 16. The deflection lumen 26 is plugged with a plug 66 of elastomeric material. A simple plug 66 made from adhesive, epoxy or urethane, or a polymer having a length 039" (1 mm) or less could be used. The distal outer sheath 34 is reflow molded in the distal segment 54 to encase the depicted components to either provide the catheter body distal end 16 having the same diameter as the catheter body 12 along its length as depicted or having a taper to a reduced diameter surrounding the distal end of the delivery lumen liner 44.

The steerable catheter 200 is advanced through the tortuous pathway until the catheter body distal end 16 is advanced to the implantation site for implantation of a cardiac lead. The cardiac lead is then advanced through the hub delivery lumen 62 and the catheter delivery lumen 24 to eject the cardiac lead distal end at the implantation site where it is fixed in any of the manners known in the art.

In this example, the catheter body 12 can preferably have an outer diameter of about 0.118 inches (3.0 mm). The delivery lumen diameter is preferably about 0.072 inches (1.82 mm) and the deflection lumen diameter is preferably about 0.025 inches (0.64 mm).

Over-the Wire Steerable Catheter

Figure 10:
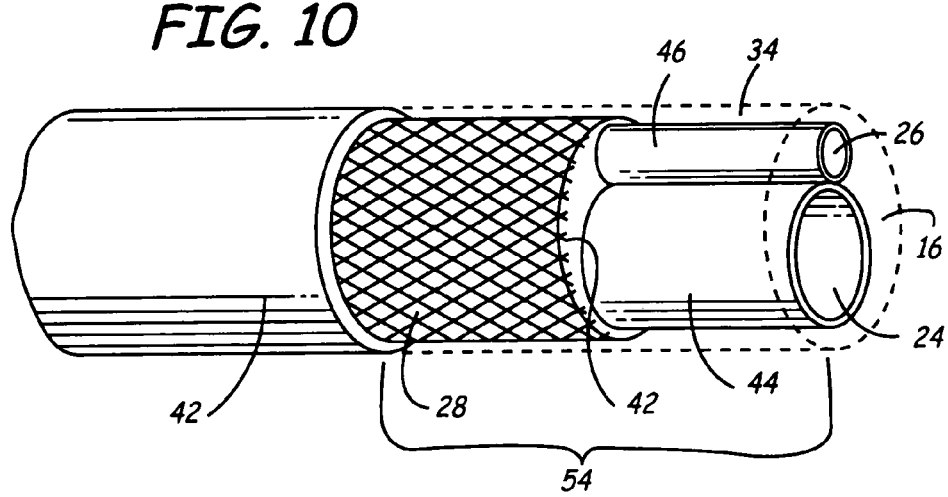
FIG. 10 is a perspective view of the distal segment of the catheter body of FIG. 9 illustrating the open deflection lumen distal end enabling over-the-wire advancement of the steerable catheter in an over-the-wire manner.
Figure 9:
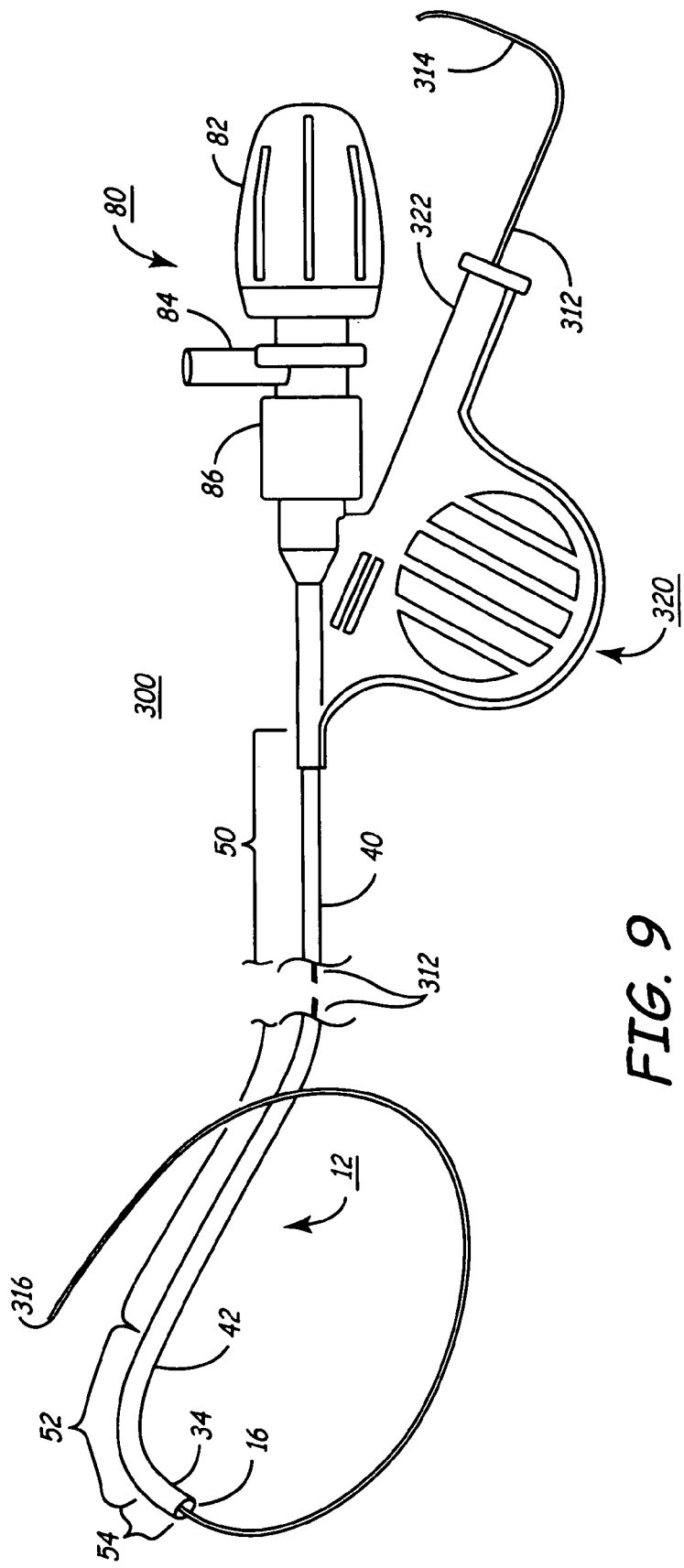
FIG. 9 is a plan view of an over-the-wire steerable catheter formed of the catheter body of FIGS. 1 and 2 and a universal hub configured to be advanced over a guide wire inserted through the deflection lumen comprising a guide wire lumen.

The steerable catheter 300 illustrated in FIG. 9 comprises the catheter body 12 constructed at the catheter body distal end 16 as depicted in FIG. 10 and attached at the catheter body proximal end 14 to the universal hub 320. Universal hub 320 is formed of hub body 60 depicted in cross-section in FIG. 13 and described above, modified by the depicted elongated side port extension 322 and incorporating the hemostasis valve 80. The deflection mechanism 30 of the steerable catheter 300 illustrated in FIG. 6 comprises a guide wire 310 in this embodiment.

The guide wire 310 can take any of the known forms having a diameter of about 0.018 inches (0.46 mm) and a length of about 40 inches (about 100 cm) to 60 inches (about 150 cm) between guide wire proximal end 314 and guide wire distal end 316. The guide wire 310 is advanced through the tortuous pathway and the catheter body 12 is advanced over the guide wire 310. The guide wire 310 passes through the hub deflection lumen 64 and the catheter body deflection lumen 26 that collectively comprise a guide wire lumen. The steerable catheter 300 is advanced over the guide wire 310 until the catheter body distal end 16 is advanced to the implantation site for implantation of a cardiac lead. The cardiac lead is then advanced through the hub delivery lumen 62 and the catheter delivery lumen 24 to eject the cardiac lead distal end at the implantation site where it is fixed in any of the manners known in the art.

In this embodiment, the catheter body distal segment 54 illustrated in FIG. 10 only comprises a distal segment of both the delivery lumen liner 44 and the deflection lumen liner 46 embedded within distal outer sheath 34 (shown in broken lines to illustrate interior components). The distal outer sheath 34 is reflow molded in the distal segment 54 to encase the depicted components to provide the catheter body distal end 16 having the same diameter as the catheter body 12 along its length as depicted or having a slight taper to a reduced diameter surrounding the distal ends of the delivery lumen liner 44 and the deflection lumen liner 46.

In this example, the catheter body 12 can preferably have an outer diameter of about 0.118 inches (3.0 mm). The delivery lumen diameter is preferably about 0.072 inches (1.82 mm) and the deflection lumen diameter is preferably about 0.025 inches (0.64 mm).

Shape Memory Alloy Steerable Catheter

Figure 11:
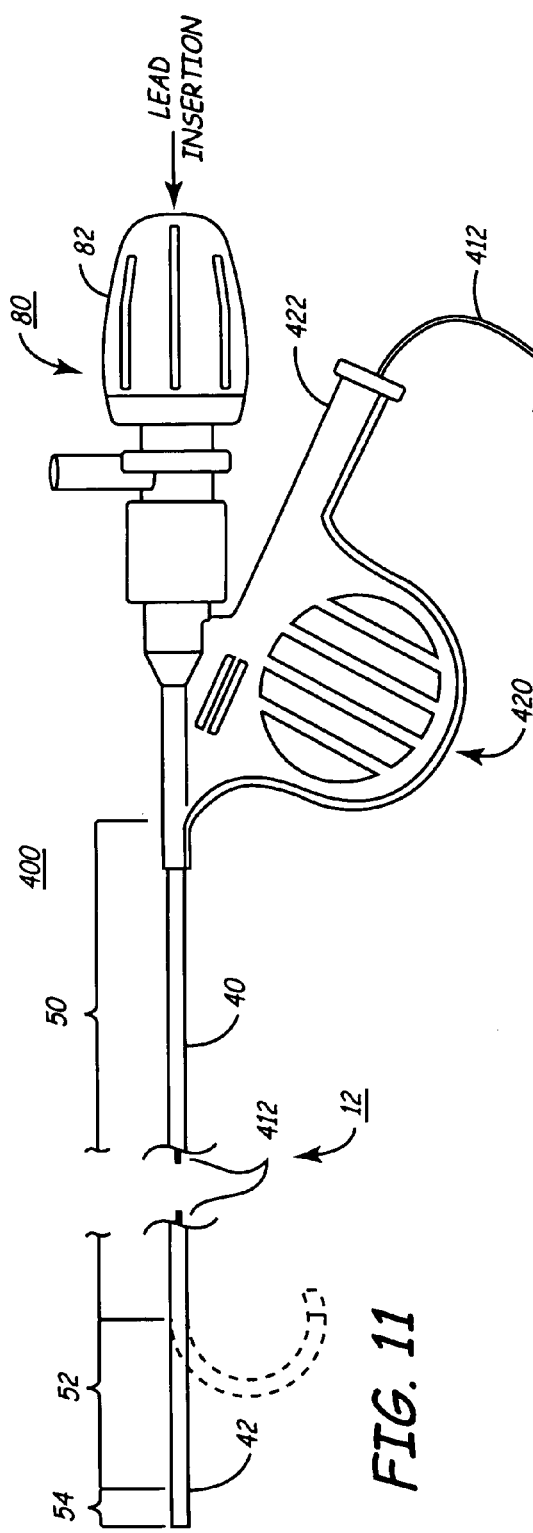
FIG. 11 is a plan view of a deflectable steerable catheter formed of the catheter body of FIGS. 1 and 2 and a universal hub incorporating a temperature responsive shape memory alloy member incorporated into the catheter body intermediate segment.
Figure 12:
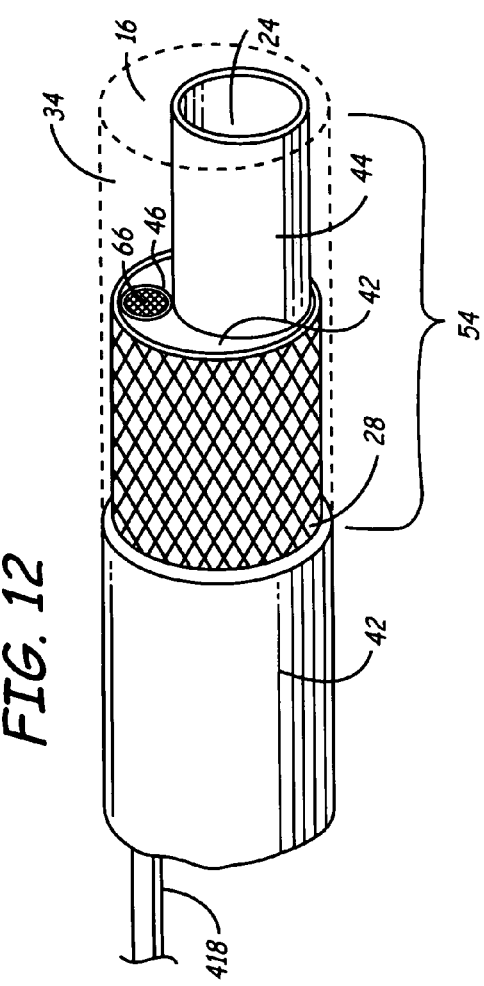
FIG. 12 is a perspective view of the distal segment of the catheter body of FIG. 11 illustrating the temperature responsive shape memory alloy member incorporated into the catheter body intermediate segment for inducing a bend in the intermediate segment.

The steerable catheter 400 illustrated in FIG. 11 comprises the catheter body 12 modified at the catheter body distal end 16 as depicted in FIG. 12 and attached at the catheter body proximal end 14 to the universal hub 280. Universal hub 280 is formed of hub body 60 depicted in cross-section in FIG. 13 and described above, modified by the depicted elongated side port extension 282 and incorporates the hemostasis valve 80. The deflection mechanism 30 of the steerable catheter 400 illustrated in FIG. 11 comprises a resistance heated shape memory alloy element 418 depicted in FIG. 12.

The shape memory alloy element 418 is inserted into the deflection lumen 26 within the intermediate segment 52 and is electrically connected through conductors extending proximally through the deflection lumen 26, the hub deflection lumen 64 and the cable 418 extending from side port 282 to an electrical connector 414. The shape memory alloy element 418 assumes a straight shape when electrical current is not applied to it and assumes a bend when electrical current is applied through connector 414 and cable 412 as shown in broken lines in FIG. 11.

Again, the catheter body distal segment 54 illustrated in FIG. 12 only comprises a distal segment of the delivery lumen liner 44 and the distal outer sheath 34 (shown in broken lines to illustrate interior components). The deflection lumen liner 46 is truncated proximal to the catheter body distal end 16. The deflection lumen 26 is plugged with a plug of elastomeric material 66 that can be created in the reflow molding of the distal outer sheath 34 into the deflection lumen 26. The distal outer sheath 34 is reflow molded in the distal segment 54 to encase the depicted components to either provide the catheter body distal end 16 having the same diameter as the catheter body 12 along its length as depicted or having a taper to a reduced diameter surrounding the distal end of the delivery lumen liner 44.

The steerable catheter 400 is advanced through the tortuous pathway until the catheter body distal end 16 is advanced to the implantation site for implantation of a cardiac lead. The cardiac lead is then advanced through the hub delivery lumen 62 and the catheter delivery lumen 24 to eject the cardiac lead distal end at the implantation site where it is fixed in any of the manners known in the art.

In this example, the catheter body 12 can preferably have an outer diameter of about 0.118 inches (3.0 mm). The delivery lumen diameter is preferably about 0.086 inches (2.18 mm) and the deflection lumen diameter is preferably about 0.013 inches (0.33 mm).

Other Catheter Embodiments:

Catheters formed in accordance with the teachings of the present invention can further include relatively simple introducers, sheaths, cannulas, urologic catheters, drainage catheters and tubes, and the like, as well as more complex, steerable coronary sinus (CS) catheters, angiography catheters, catheters for locating pulmonary veins, intra-cardiac echo (ICE) catheters, aortic bypass catheters, PTCA and stent delivery balloon catheters, other balloon catheters, EP mapping and/or RF ablation catheters and the like in a wide variety of lengths and diameters. In a relatively simple catheter having only one lumen, the single lumen is defined by a catheter lumen liner formed of an above-described no yield elastomer.

CONCLUSION

All patents and publications identified herein are hereby incorporated by reference in their entireties.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. An elongated multi-lumen steerable catheter comprising:
   a catheter body extending between a catheter body proximal end and a catheter body distal end and having a proximal segment, a bendable intermediate segment and a distal segment, the catheter body further comprising:
   an outer sheath extending between the catheter body proximal end and the catheter body distal end;
   a deflection lumen extending within the outer sheath from a deflection lumen proximal end opening to the catheter body distal end; and
   a delivery lumen extending within the outer sheath between a delivery lumen proximal end opening and a delivery lumen distal end opening at the catheter body distal end, the delivery lumen defined by a delivery lumen liner formed of an elastomer extending through the proximal segment, the bendable intermediate segment, and the distal segment of the catheter body;
   a hub mounted to the catheter body proximal end; and
   a deflection mechanism introduced within the deflection lumen selectively operable at the hub inducing a bend in the intermediate segment, wherein the outer sheath comprises a proximal outer sheath segment formed of a first thermoplastic material having a first flexural modulus extending the length of the catheter body proximal segment, an intermediate sheath segment formed of a second thermoplastic material having a second flexural modulus extending the length of the catheter body intermediate segment, and a distal sheath formed of a third thermoplastic material having a third flexural modulus lower than the first flexural modulus and second flexural modulus, the distal sheath extending the length of the catheter body distal segment.

2. The steerable catheter of claim 1, wherein the outer sheath distal segment embedding the distal segment of the delivery lumen liner has a flexural modulus $\leq 1,300$ psi.

3. The steerable catheter of claim 2, wherein the delivery lumen liner is formed having a 51D Shore durometer and a flexural modulus of about 25 ksi.

4. The steerable catheter of claim 1, wherein the catheter body further comprises:
   a deflection lumen liner; and
   a wire braid extending around and over the delivery lumen liner and the deflection lumen liner through the length of the proximal segment and the bendable intermediate segment of the catheter body.

5. The steerable catheter of claim 1, wherein the deflection mechanism comprises a stylet having a stylet wire adapted to be inserted through the deflection lumen to induce a bend in the intermediate segment of the catheter body corresponding to a bend in the stylet wire to steer the catheter body distal end through an access pathway of the body.

6. The steerable catheter of claim 1, wherein the deflection mechanism comprises a guidewire adapted to be passed through the deflection lumen to enable over-the-wire advancement of the steerable catheter through an access pathway of the body.

7. The steerable catheter of claim 1, wherein the deflection mechanism comprises a pull wire having a pull wire extending from the hub through the deflection lumen to the catheter body distal adapted to be retracted to induce a bend in the intermediate segment of the catheter body to steer the catheter body distal end through an access pathway of the body.

8. An elongated multi-lumen steerable catheter comprising:
   a catheter body extending between a catheter body proximal end and a catheter body distal end and having a proximal segment, a bendable intermediate segment and a distal segment, the catheter body further comprising:
   an outer sheath extending between the catheter body proximal end and the catheter body distal end;
   a deflection lumen extending within the outer sheath from a deflection lumen proximal end opening to the catheter body distal end; and
   a delivery lumen extending within the outer sheath between a delivery lumen proximal end opening and a delivery lumen distal end opening at the catheter body distal end, the delivery lumen defined by a delivery lumen liner formed of an elastomer extending through the proximal segment, the bendable intermediate segment, and the distal segment of the catheter body;
   a hub mounted to the catheter body proximal end; and
   a deflection mechanism introduced within the deflection lumen selectively operable at the hub inducing a bend in the intermediate segment, wherein the delivery lumen liner is formed having a 51D Shore durometer and a flexural modulus of about 25 ksi.

9. An elongated multi-lumen steerable catheter comprising:
   a catheter body extending between a catheter body proximal end and a catheter body distal end and having a proximal segment, a bendable intermediate segment and a distal segment, the catheter body further comprising:
   an outer sheath extending between the catheter body proximal end and the catheter body distal end;
   a deflection lumen extending within the outer sheath from a deflection lumen proximal end opening to the catheter body distal end; and
   a delivery lumen extending within the outer sheath between a delivery lumen proximal end opening and a delivery lumen distal end opening at the catheter body distal end, the delivery lumen defined by a delivery lumen liner formed of an elastomer extending through the proximal segment, the bendable intermediate segment, and the distal segment of the catheter body;
   a hub mounted to the catheter body proximal end; and a deflection mechanism introduced within the deflection lumen selectively operable at the hub inducing a bend in the intermediate segment, wherein the catheter body further comprises:
   a deflection lumen liner; and
   a wire braid extending around and over the delivery lumen liner and the deflection lumen liner through the length of the proximal segment and the bendable intermediate segment of the catheter body.

10. An elongated multi-lumen steerable catheter comprising:

a catheter body extending between a catheter body proximal end and a catheter body distal end and having a proximal segment, a bendable intermediate segment and a distal segment, the catheter body further comprising:
an outer sheath extending between the catheter body proximal end and the catheter body distal end;
a deflection lumen extending within the outer sheath from a deflection lumen proximal end opening to the catheter body distal end; and
a delivery lumen extending within the outer sheath between a delivery lumen proximal end opening and a delivery lumen distal end opening at the catheter body distal end, the delivery lumen defined by a delivery lumen liner formed of an elastomer extending through the proximal segment, the bendable intermediate segment, and the distal segment of the catheter body;
a hub mounted to the catheter body proximal end; and a deflection mechanism introduced within the deflection lumen selectively operable at the hub inducing a bend in the intermediate segment, wherein the deflection mechanism comprises a resistance heated shape memory alloy element disposed within the deflection lumen within the catheter body intermediate segment and electrical conductors extending through the deflection lumen to the resistance heated shape memory alloy element to apply electrical energy to and resistance heat the shape memory alloy element to induce a bend in the resistance heated shape memory alloy element to steer the catheter body distal end through an access pathway of the body.

11. An elongated catheter comprising:
a catheter body extending between a catheter body proximal end and a catheter body distal end, the catheter body comprises a stiff proximal segment, a flexible intermediate segment and a soft distal segment, the catheter body further comprising:
an outer sheath extending between the catheter body proximal end and the catheter body distal end; and
a catheter lumen liner extending within the outer sheath from a catheter lumen proximal end opening to a catheter lumen distal end opening at the catheter body distal end, the catheter lumen liner formed of an elastomer, and
a hub mounted to the catheter body proximal end, wherein the outer sheath comprises a proximal outer sheath segment formed of a first thermoplastic material having a first flexural modulus extending the length of the catheter body proximal segment, an intermediate sheath segment formed of a second thermoplastic material having a second flexural modulus extending the length of the catheter body intermediate segment, and a distal sheath formed of a third thermoplastic material having a third flexural modulus lower than the first flexural modulus and second flexural modulus, the distal sheath extending the length of the catheter body distal segment.

12. The steerable catheter of claim 11, wherein the outer sheath distal segment embedding the distal segment of the delivery lumen liner has a flexural modulus $\leq 1,300$ psi.

13. The steerable catheter of claim 12, wherein the catheter lumen liner is formed having a 51D Shore durometer and a flexural modulus of about 25 ksi.

14. The steerable catheter of claim 11, wherein the catheter body further comprises a wire braid extending around and over the catheter lumen liner through the length of the proximal segment and the bendable intermediate segment of the catheter body.

15. The steerable catheter of claim 11, wherein the catheter lumen liner is formed having a 51D Shore durometer and a flexural modulus of about 25 ksi.

16. An elongated catheter comprising:
a catheter body extending between a catheter body proximal end and a catheter body distal end, the catheter body comprises a stiff proximal segment, a flexible intermediate segment and a soft distal segment, the catheter body further comprising:
an outer sheath extending between the catheter body proximal end and the catheter body distal end; and
a catheter lumen liner extending within the outer sheath from a catheter lumen proximal end opening to a catheter lumen distal end opening at the catheter body distal end, the catheter lumen liner formed of an elastomer, and a hub mounted to the catheter body proximal end, wherein the catheter body further comprises a wire braid extending around and over the catheter lumen liner through the length of the proximal segment and the bendable intermediate segment of the catheter body.

17. An elongated catheter comprising:
a catheter body extending between a catheter body proximal end and a catheter body distal end, the catheter body comprises a stiff proximal segment, a flexible intermediate segment and a soft distal segment, the catheter body further comprising:
an outer sheath extending between the catheter body proximal end and the catheter body distal end; and
a catheter lumen liner extending within the outer sheath from a catheter lumen proximal end opening to a catheter lumen distal end opening at the catheter body distal end, the catheter lumen liner formed of an elastomer, and
a hub mounted to the catheter body proximal end, wherein the catheter lumen liner is formed having a 51D Shore durometer and a flexural modulus of about 25 ksi.

* * * * *

UNITED STATES PATENT AND TRADEMARK OFFICE
CERTIFICATE OF CORRECTION

PATENT NO. : 7,037,290 B2
APPLICATION NO. : 10/318624
DATED : May 2, 2006
INVENTOR(S) : Gardeski et al.

It is certified that error appears in the above-identified patent and that said Letters Patent is hereby corrected as shown below:

Column 17, line 49, please delete "$\leqq$ 1,300 psi." and insert --$\leq$ 1,300 psi.--

Column 20, line 6, please delete "$\leqq$ 1,300 psi." and insert --$\leq$ 1,300 psi.--

Signed and Sealed this

Fifth Day of June, 2007

JON W. DUDAS
*Director of the United States Patent and Trademark Office*